United States Patent
Costin

(10) Patent No.: US 6,251,896 B1
(45) Date of Patent: Jun. 26, 2001

(54) COMPOSITIONS AND METHODS FOR THE MANAGEMENT OF CROHN'S DISEASE

(75) Inventor: James C. Costin, Belle Mead, NJ (US)

(73) Assignee: Carter-Wallace, Inc., New York, NY (US)

(*) Notice: Subject to any disclaimer, the term of this patent is extended or adjusted under 35 U.S.C. 154(b) by 0 days.

(21) Appl. No.: 09/535,477

(22) Filed: Mar. 24, 2000

Related U.S. Application Data

(60) Provisional application No. 60/125,880, filed on Mar. 24, 1999.

(51) Int. Cl.$^7$ ................................................. A61K 31/54
(52) U.S. Cl. ..................................... 514/222.5; 514/222.2
(58) Field of Search ............................... 514/222.2, 222.5

(56) References Cited

PUBLICATIONS

Gardiner et al. "Enteral and parenteral anti-endotoxin treatment in experimental colitis." HepatoGastroenterology, (Dec. 1994) 41(6) 554–8 Journal code: GA7. ISSN: 0172–6390.*

\* cited by examiner

*Primary Examiner*—Theodore J. Criares
*Assistant Examiner*—Jennifer Kim
(74) *Attorney, Agent, or Firm*—Allen R. Kipnes; Kenneth Watov; Watov & Kipnes, P.C.

(57) ABSTRACT

The present invention relates to a method of treating a human infected with Crohn's disease comprising enterally administering to the individual in need of such treatment an effective amount of a composition comprising 4,4'-methylenebis-(tetrahydro-1,2,4-thiadiazine)-1,1,1',1'-tetraoxide, commonly known as taurolidine.

8 Claims, No Drawings

COMPOSITIONS AND METHODS FOR THE MANAGEMENT OF CROHN'S DISEASE

RELATED APPLICATION

This application claims the benefit of U.S. Provisional Application No. 60/125,880 filed Mar. 24, 1999.

FIELD OF THE INVENTION

The present invention relates to novel compositions and their use. In particular, this invention relates to the use of 4,4'-methylenebis-(tetrahydro-1,2,4-thiadiazine)-1,1,1',1'-tetraoxide, commonly known as taurolidine in the treatment of Crohn's disease.

BACKGROUND OF THE INVENTION

Crohn's disease, an idiopathic inflammatory bowel disease, is characterized by chronic inflammation at various sites in the gastrointestinal tract. While Crohn's disease most commonly affects the distal ileum and colon, it may manifest itself in any part of the gastrointestinal tract from the mouth to the anus and perianal area. Up to the present time, all drugs used in the treatment of Crohn's disease function as prophylactics against the symptoms of Crohn's disease, i.e. inflammation as opposed to being curatives. Established chronic Crohn's disease is characterized by life long exacerbations.

Since its first documentation more than two hundred years ago, the incidence of Crohn's disease has increased markedly and universally throughout the world's populations. The disease is nondiscriminating with respect to sex showing relatively equal incidence of Crohn's disease in both sexes. The anatomic distribution of Crohn's disease has changed in recent years, with an increase in the incidence of large bowel disease. In addition, studies have shown that in the elderly, isolated colonic Crohn's disease is more common than in patients whose disease presents at a younger age, i.e. ages 60 and lower.

The etiology of Crohn's disease is unknown. Immunologic factors have been examined; possible infectious agents have included various enteric bacteria, viruses and chlamydiae. Dietary factors, i.e. fiber-poor diet and stress have also been considered. Mycobacteria is now receiving most focus. The isolation of several different mycobacterial species from Crohn's diseased patients and the knowledge that *M. paratuberculosis* causes a granulomatous intestinal disease in ruminants has generated keen interest in this organism.

Long standing Crohn's disease predisposes patients to cancer, the most common type being adenocarcinoma which generally occurs in areas where Crohn's disease has been present for many years. Both small bowel and colon cancers occur with increased incidence in Crohn's disease. The increased cancer risk in Crohn's disease is most definitely established for cases of cancer of the ileum, for which the relative risk in Crohn's disease is at least 100-fold greater than in an age/sex matched control population.

SUMMARY OF THE INVENTION

The present invention relates to compositions and methods for the management of Crohn's disease. More particularly, the present invention relates to the administration of taurolidine to combat the inflammatory effects and bacterial causes of Crohn's disease.

DETAILED DESCRIPTION OF THE INVENTION

Taurolidine occurs as a white to off-white powder having the molecular formula —$C_7H_{16}N_4O_4S_2$.

Taurolidine's general characteristics include acceptable stability in the solid state when stored at ambient conditions, melting with decomposition at approximately 170° C. and the following solubility in aqueous solutions and organic solvents.

| | |
|---|---|
| Water | 1% at 20° C. |
| Dilute HCl | soluble |
| Dilute NaOH | soluble |
| $CHCl_3$ | insoluble |
| EtOH | sparingly soluble |
| DMF | 1 g in 2 mL/ca. 60° C. |
| Acetone | 1 g in 120 mL/Boiling |
| Ethanol | 1 g in 130 mL/Boiling |
| Methanol | 1 g in 170 mL/Boiling |
| Ethyl Acetate | 1 g in 200 mL/Boiling |

A saturated solution of taurolidine in deionized water has a pH of 7.4. The apparent partition coefficient of taurolidine between octanol and water (buffered at pH 7.2) is approximately 0.13 and would therefore not be predicted to accumulate to any significant extent in fatty tissues.

The synthesis of taurolidine is covered in a number of patents including U.S. Pat. No. 3,423,408; Switzerland No. 482,713 and United Kingdom No.1,124,285 and is carried out in five stages:

Potassium phthalimidoethane sulphonate is prepared from taurine, phthalic anhydride, glacial acetic acid and potassium acetate;

Potassium phthalimidoethane sulphonate is then converted to phthalimidoethane sulphonylchloride by chlorination with phosphorous oxychloride;

Phthalimidoethane sulphonylchloride is reacted with ammonia to form phthalimidoethane sulphonamide;

Phthalimidoethane sulphonylchloride is reacted with hydrazine hydrate and in the subsequent hydrazinolysis to form taurinamide hydrochloride; and Taurolidine is prepared from taurinamide hydrochloride and formaldehyde.

The antimicrobial actions of taurolidine have been described in co-pending U.S. patent application Ser. No. 09/151,885 filed Sep. 11, 1998 and in U.S. Pat. No. 3,423,408 and elsewhere in the literature. In addition, the following United States Patents describe various uses for and compositions containing taurolidine: U.S. Pat. No. 4,107,305, treatment of endotoxaemia; U.S. Pat. No. 4,337,251, elimination of adhesion formation as a result of surgery; U.S. Pat. No. 4,587,268, resorbable aqueous gels; U.S. Pat. No. 4,604,391, prevention of the occurrence of osteitis or osteomyelitis; U.S. Pat. No. 4,626,536, combating toxic proteins or peptides in the blood; U.S. Pat. No. 4,772,468, treatment of bone cavities; and U.S. Pat. No. 4,882,149, directed to methods for filling congenital, surgical or traumatic defects with compositions comprising natural bone mineral having absorbed therein/thereon taurolidine.

Taurolidine's mechanism of action unlike that of known antibiotics is based on a chemical reaction. While not being bound by any theory, during the metabolism of taurolidine to taurinamide and ultimately taurine and water, methylol groups are liberated which chemically react with the mureins in the bacterial cells walls this results in the denaturing of the complex polysaccharide and liposaccharide components of the bacterial cell wall as well as changing the double stranded DNA of the plasmid to a denatured or single stranded DNA.

Taurolidine has been shown to be safe and well tolerated at systemic doses exceeding 40 g/day and cumulative doses up to and exceeding 300 g.

It has long been the goal of the pharmaceutical industry to produce antibiotic medicinal substances that have the power to kill—or at least to arrest the growth of—many disease causing mycobacteria such as those associated with Crohn's disease.

In general, the compositions of the present invention can be readily utilized in variety of pharmaceutical formulations, preferably formulations which release taurolin in the gut. The disclosed medicament may be used alone or in combination with a pharmacologically and/or nutritionally acceptable carrier.

The formulations of taurolidine generally utilized are sterile solutions containing about 0.5%, 1.0%, 2.0% or about 4.0% taurolidine.

The compositions of the present invention for the management of Crohn's disease may take any of a variety of forms as noted, however, in terms of ability to deliver the active material to the target site of action, i.e. the gastrointestinal tract, it is preferred to use enema, suppository, tablet, capsule, solution or suspension formulations. A particularly preferred form is a delayed or sustained release form which coats microgranules of taurolidine with a semipermeable membrane such as ethyl cellulose for gradual pH-dependent release throughout the gut.

Solid carriers and diluents suitable for use include sugars such as lactose and sucrose, cellulose derivatives such as carboxymethyl cellulose, ethylcellulose, methylcellulose, etc., gelatin including hard and soft gelatin capsules, talc, cornstarch, stearic acid and magnesium stearate.

Suspension formulations may additionally contain benzoic acid, coloring, natural and artificial flavors, glycerin, kaolin, magnesium, aluminum silicate, methyl paraben, pectin, purified water, saccharin, sodium hydroxide and sucrose.

The percentage of taurolidine in the composition can be varied over wide limits and the quantity of medicament furnished by each individual tablet, capsule, solution or suspension is relatively unimportant since the indicated daily dose can be reached by administering either one or a plurality of capsules, tablets or suspensions.

The following non-limiting Examples are provided to illustrate further the present invention:

EXAMPLE 1

Solution

Taurolidine: 400 g
Polyvinylpyrrolidone: 100 g
Sterile Water to: 20 liters

15 Liters double distilled pyrogen free water are filled into a 25 liter glass vessel with stirrer and intensive reflux device and heated to 50° C. with stirring. The taurolidine 400 g is added followed by polyvinylpyrrolidone 1000 g. After dissolution, the solution is cooled and the pH adjusted to 6.0 with a few drops of 0.1N hydrochloric acid. The solution is then passed through an adsorption filter to remove microorganisms and pyrogens and through a sterilising millipore filter before being filled into 100 ml vials which are finally autoclaved.

EXAMPLE 2

Solution

Taurolidine: 990 g
Sterile Water ad: 22 liters

The taurolidine is dissolved in the sterile water and filled into sterile bottles, 250 ml in each.

EXAMPLE 3

Tablet

Taurolidine: 500 g
Amylum maydis: 60 g
Kollidone 25: 50 g (polyvinylpyrrolidone)
Plasdon XL: 20 g
Magnesium stearate: 6 g
Distilled water: 200 g 1000 tablets, each containing 500 mg taurolidine, are produced by conventional means using the above formulation.

In an alternative tablet formulation, the amylum maydis is replaced by 60 g amylum orizae.

EXAMPLE 4

Solution

Taurolidine: 440 g
Pharmaceutical gelatin: 88 g
Sodium chloride: 99 g
Sterile water to: 22 liters The components are dissolved in the sterile water, if necessary using gentle warming and sonication. The solution is then filled into sterile bottles, 500 ml in each.

Taurolidine has been employed as primary therapy for active Crohn's disease in patients without complication.

EXAMPLE 5

A patient with Crohn's disease is treated with about 10 to about 500 mg/kg body weight taurolidine administered orally, intravenously or intraperitoneally which results in significant improvement in disease activity as measured by the Crohn's Disease Activity Index. The drug is particularly effective in the treatment of perineal disease.

The foregoing description is given for clearness of understanding of the invention only, and no unnecessary limitations should be understood therefrom, as modifications will be obvious to those skilled in the art.

I claim:

1. A method of treating a human infected with Crohn's disease comprising enterally administering to the individual in need of such treatment an effective amount of a composition comprising 4,4-methylenebis (tetrahydro-1,2,4-thiadiazine-1,2-dioxide).

2. A method according to claim 1 wherein the composition is in capsule form.

3. A method according to claim 1 wherein the composition is in tablet form.

4. A method according to claim 1 wherein the composition is in suspension form.

5. A method according to claim 1 wherein the composition is in solution form.

6. A method according to claim 1 wherein the composition is in a controlled release form.

7. A method according to claim 1 wherein the composition is in suppository form.

8. A method according to claim 1 wherein the composition is in the form of an enema.

* * * * *